(12) United States Patent
Conrad (10) Patent No.: US 11,129,626 B2
(45) Date of Patent: Sep. 28, 2021

(54) FLEXIBLE DRIVE SHAFT ASSEMBLY AND METHODS

(71) Applicant: Zimmer, Inc., Warsaw, IN (US)

(72) Inventor: Steven Conrad, Albion, IN (US)

(73) Assignee: Zimmer, Inc., Warsaw, IN (US)

( * ) Notice: Subject to any disclaimer, the term of this patent is extended or adjusted under 35 U.S.C. 154(b) by 218 days.

(21) Appl. No.: 16/202,985

(22) Filed: Nov. 28, 2018

(65) Prior Publication Data
US 2019/0159787 A1    May 30, 2019

Related U.S. Application Data

(60) Provisional application No. 62/592,050, filed on Nov. 29, 2017.

(51) Int. Cl.
*A61B 17/16*    (2006.01)
*B29C 45/16*    (2006.01)
(Continued)

(52) U.S. Cl.
CPC ...... *A61B 17/1631* (2013.01); *B29C 45/0001* (2013.01); *B29C 45/0003* (2013.01);
(Continued)

(58) Field of Classification Search
CPC .......... A61B 2017/00526; A61B 17/16; A61B 17/1613; A61B 17/1615; A61B 17/162;
(Continued)

(56) References Cited

U.S. PATENT DOCUMENTS

| 1,831,752 | A | * | 11/1931 | Reinold | ......... A47J 45/08 220/752 |
| 4,751,922 | A | * | 6/1988 | DiPietropolo | ......... B23Q 5/043 606/80 |

(Continued)

OTHER PUBLICATIONS

"European Application Serial No. 18208953.2, Response filed Dec. 3, 2019 to Extended European Search Report dated Apr. 17, 2019", 12 pages.

(Continued)

*Primary Examiner* — Zade Coley
(74) *Attorney, Agent, or Firm* — Schwegman Lundberg & Woessner, P.A.

(57) ABSTRACT

Illustrative methods of manufacturing flexible drive shaft assemblies for preparing bone can include steps such as providing, receiving or manufacturing a mold. Injecting a first polymeric material into the mold to form a coupling member, the coupling member adapted for attachment to a torque-providing driving tool. Injecting a second polymeric material into the mold to form a work member, the work member adapted to interface with the bone to prepare the bone. The method can further include injecting a third polymeric material into the mold in an overmolding process to form a flexible shaft extending from the coupling member to the work member. The assemblies resulting from such methods can include a flexible shaft that is adapted to transmit a majority of a torque received from a torque-providing driving tool through the flexible shaft. In some examples, the flexible shaft can include a solid polymeric shaft.

11 Claims, 7 Drawing Sheets

(51) Int. Cl.
  *B29C 45/00* (2006.01)
  *A61B 17/00* (2006.01)
(52) U.S. Cl.
  CPC ...... *B29C 45/0017* (2013.01); *B29C 45/1671* (2013.01); *A61B 2017/00526* (2013.01); *B29C 2045/0089* (2013.01); *B29C 2045/0093* (2013.01)
(58) Field of Classification Search
  CPC ............ A61B 17/1631; A61B 17/1637; A61B 17/1642
  See application file for complete search history.

(56) References Cited

U.S. PATENT DOCUMENTS

| | | |
|---|---|---|
| 2005/0043739 A1 | 2/2005 | Sullivan et al. |
| 2007/0093840 A1 | 4/2007 | Pacelli et al. |
| 2007/0161427 A1* | 7/2007 | White ...................... F16C 1/02 464/52 |
| 2008/0140078 A1* | 6/2008 | Nelson ............... A61B 17/1615 606/80 |
| 2010/0152739 A1 | 6/2010 | Sidebotham et al. |
| 2016/0007976 A1* | 1/2016 | Gauthier ................. A61L 31/14 428/138 |
| 2016/0346909 A1* | 12/2016 | Victor .................... A61B 90/03 |
| 2017/0100136 A1* | 4/2017 | Dougherty ......... A61B 17/1633 |

OTHER PUBLICATIONS

"European Application Serial No. 18208953.2, Extended European Search Report dated Apr. 17, 2019", 7 pgs.
"European Application Serial No. 18208953.2, Communication Pursuant to Article 94(3) EPC dated Mar. 5, 2021", 4 pgs.
"European Application Serial No. 18208953.2, Response filed Jul. 15, 2021 to Communication Pursuant to Article 94(3) EPC dated Mar. 5, 2021", 14 pages.

* cited by examiner

FLEXIBLE DRIVE SHAFT ASSEMBLY AND METHODS

CLAIM OF PRIORITY

This application claims the benefit of U.S. Provisional Patent Application Ser. No. 62/592,050, filed on Nov. 29, 2017, the benefit of priority of which is claimed hereby, and which is incorporated by reference herein in its entirety.

TECHNICAL FIELD

This document pertains generally, but not by way of limitation, to flexible orthopedic tools for removing bone from a patient, and, more particularly, to flexible drive shaft assemblies and methods related to drilling, reaming, burring, or otherwise removing the bone.

BACKGROUND

In order to secure an orthopedic implant to a bone, the surgeon can prepare one or more holes in the bone with an orthopedic driver. However, the surgeon may not have a direct access to the desired axis where the hole is to be positioned in the implant site, such as at an acetabulum of a patient. In such an example, the surgeon can couple an orthopedic tool such as a flexible drive shaft assembly to the orthopedic driver. The flexible drive shaft assembly allows the surgeon to drill a hole in the bone (or otherwise prepare a bone surface) along a desired axis that is not directly accessible and that is different than the driving axis of the orthopedic driver.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

As discussed above, in order to secure an orthopedic implant to a bone, the surgeon can prepare one or more holes in the bone with an orthopedic driver. However, the surgeon may not have a direct access to the desired axis where the hole is to be positioned in the implant site, such as at an acetabulum of a patient. Described herein are flexible orthopedic tools, including flexible drive shafts assemblies and methods for preparing a bone of the patient. Preparing a bone can include drilling, reaming, burring and other related methods. The surgeon can couple a flexible drive shaft assembly to the orthopedic driver. The flexible drive shaft assembly allows the surgeon to drill a hole in the bone along a desired axis that is not directly accessible and that is different than the driving axis of the orthopedic driver.

One of the challenges of flexible drive shaft assemblies is that they are expensive to manufacture and are therefore cleaned and re-used for multiple patients. In addition, these flexible drive shaft assemblies, because of their complex design, can be difficult to clean and sterilize.

Improved flexible drive shaft assemblies and methods of forming flexible drive shaft assemblies are described herein. The assemblies and methods disclosed herein can dramatically reduce the cost to manufacture such assemblies. Because the cost to manufacture the flexible drive shaft assembly is lower, the assembly can be disposed of without needing to be cleaned and re-used. Having a new and unused flexible drive shaft assembly for each patient reduces the cost and hassle of cleaning the assembly. The rate of infection is also reduced because cross-contamination from patient to patient is eliminated.

Figure 1A:
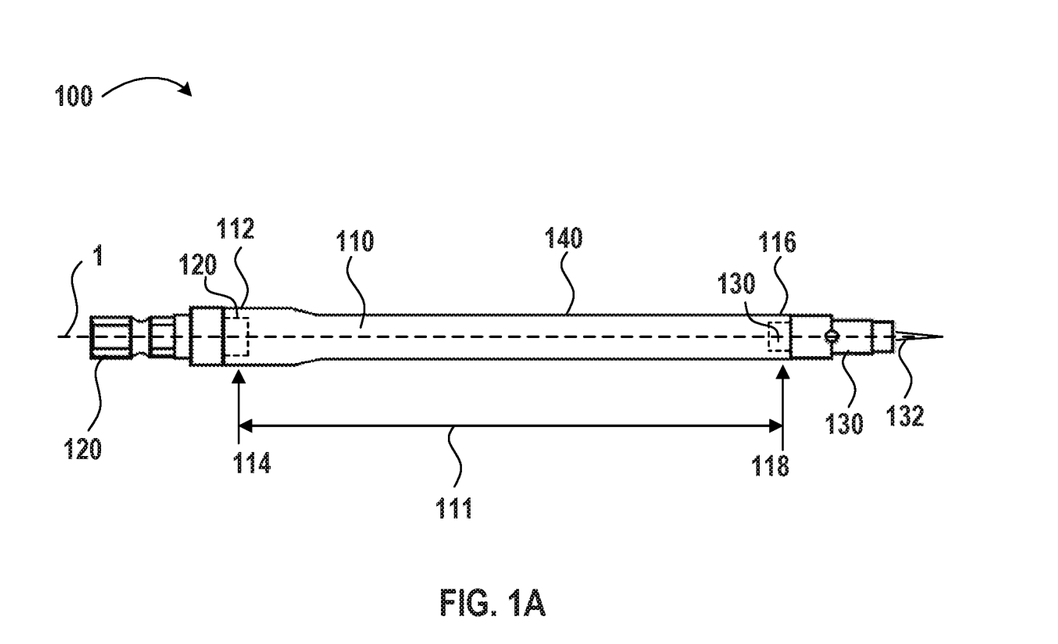
FIG. 1A is a side view of an illustrative flexible drive shaft assembly in an unbent state, in accordance with at least one example.
Figure 1B:
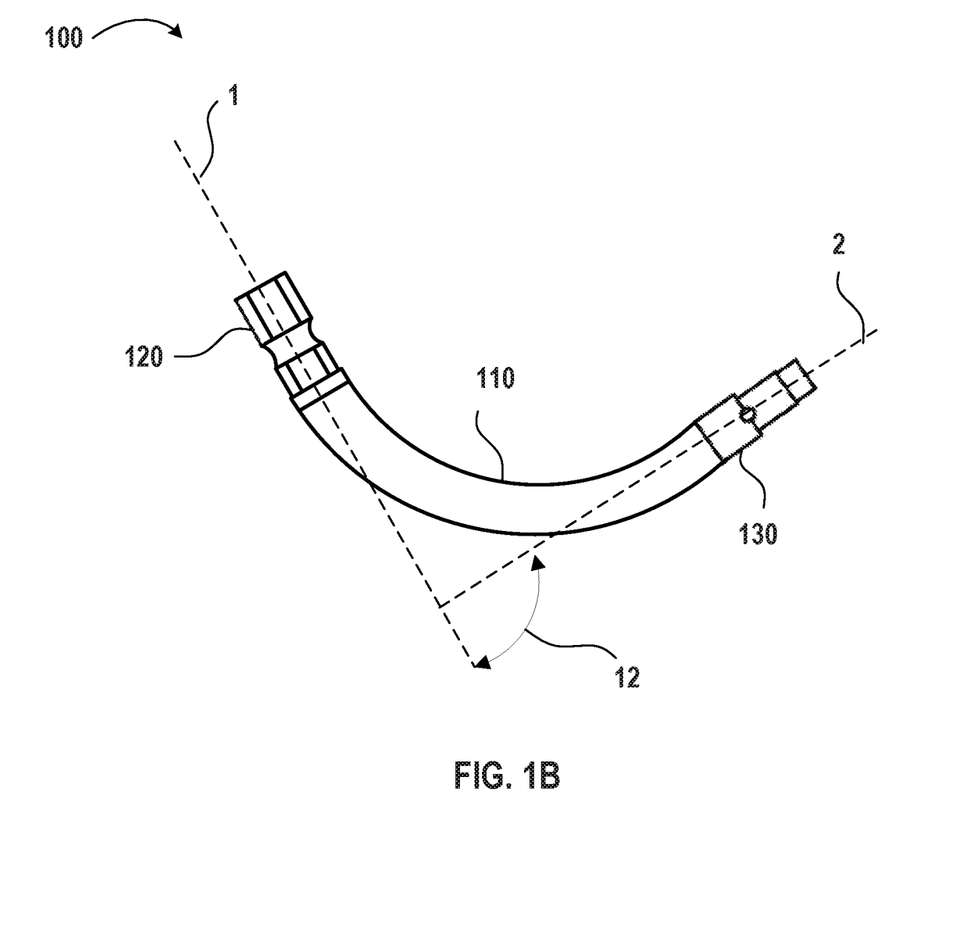
FIG. 1B is a side view of the illustrative flexible drive shaft assembly of FIG. 1A in a bent state, in accordance with at least one example.

FIG. 1A shows a side view of an illustrative flexible drive shaft assembly 100 (hereinafter, assembly) in an unbent state, while FIG. 1B shows a side view of the assembly 100 in a bent state.

As shown in FIG. 1B, the assembly 100 can be configured to be bent at a bend angle 12. The assembly 100 can be configured to transmit torque in both the unbent and bent states. Furthermore, the assembly 100 can be configured to transmit torque in the bent state, without the need of a guide, separate structure, or secondary element to direct or control the angle of the bend. The assembly 100 can be adapted to flexibly bend into and out of a bent state while transmitting torque.

The example assembly 100 can include a flexible shaft 110 positioned between and coupled to a coupling member 120 and a work member 130. The coupling member 120 can be configured to be coupled to a torque-providing driving tool (e.g., a driver) to receive rotational motion and torque from the driver. The coupling member 120 can be adapted to receive torque from the torque-providing driving tool and to transmit the torque to the flexible shaft 110.

The work member 130 can include a work element 132 or be attachable to a work element 132 such as a drill bit for drilling a hole in a bone. The work member 130 can receive rotational motion and torque from the flexible shaft 110 and transmit rotational motion and torque to the work element 132 to prepare the bone.

In the unbent state, the assembly 100 can be described as extending along a longitudinal axis 1 (FIG. 1A). In the bent state (FIG. 1B), the bend angle can be defined as the angle that the flexible shaft 110 can be bent to allow the coupling member 120 and the work member 130 to extend along separate, but intersecting axes (e.g., 1, 2, FIG. 1B) while still transferring torque from the coupling member 120 to the work member 130 through the flexible shaft 110.

In other words, as shown in FIG. 1A, the assembly 100 can extend in line with a longitudinal axis 1 in the unbent state. Or, as shown in FIG. 1B, the assembly 100 can be bent such that a portion of the assembly 100 extends away from the longitudinal axis 1. The bend angle 12 can be described as the angle between the longitudinal axis 1 (e.g. axis along the coupling member) and the work axis 2 (e.g., axis along the work member).

In some examples, the bend angle 12 can be at least 10 degrees off of the longitudinal axis 1. In some examples, the bend angle 12 can be in a range between about 10 degrees and about 90 degrees off of the longitudinal axis 1, or less than 90 degrees. In some examples, the bend angle 12 can be in a range between 20 and 80 degrees, or less than 80 degrees. A range of suitable bend angles can vary with the particular surgical procedure to be performed.

Figure 1C:
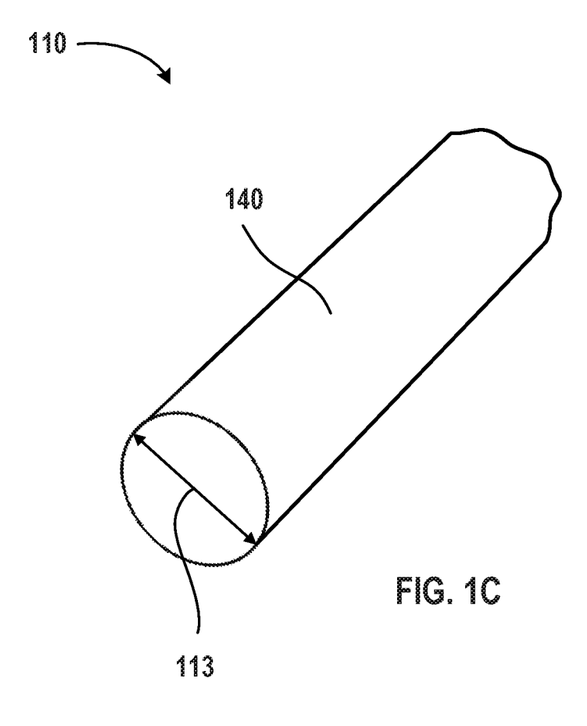
FIG. 1C is a perspective view of a portion of an illustrative flexible shaft of the flexible drive shaft assembly of FIG. 1A, in accordance with at least one example.

As shown in FIG. 1A, the flexible shaft 110 can be formed by an overmolding process. For example, the overmold 140 can form the flexible shaft 110 and can cover a portion of the coupling member 120 and a portion of the work member 130. In some examples, and as shown in FIG. 1A, the entire (e.g., all, substantially all) of the flexible shaft 110 can be formed by the overmold 140. In some examples, the flexible shaft 110 can include a solid polymeric shaft formed entirely by an overmolding process. FIG. 1C illustrates a perspective view of an example of a portion of the flexible shaft 110 including an overmold 140 having a solid overmolded diameter 113.

The overmold 140, can for example, be formed of a soft and malleable polymer such as silicone, but other suitable polymers having characteristics similar to silicone can also be used including, but not limited to, thermoplastic polyurethane. The overmold 140 that forms the flexible shaft 210 can carry substantially all the load received from a torque-providing driver at the coupling member 120 and transfer the load to the work member 130. For example, the overmold 140 can carry all of the load, the majority of the load or 90-100% of the load (e.g., torque and rotational motion).

The assembly 100 can include a first overmolded connection 112 at a first end portion 114 of the flexible shaft 110 and a second overmolded connection 116 at the second end portion 118 of the flexible shaft 110. The first overmolded connection 112 can include an overmold of the flexible shaft 110 onto the coupling member 120. The second overmolded connection 116 can include an overmold of the flexible shaft 110 onto the work member 130. Between the first and second overmolded connections 112, 116, the flexible shaft 110 can be formed as a continuous, solid shaft formed by an overmolding process. In some examples, the entire flexible shaft length 111 can be formed as a continuous, solid, polymeric overmold 140. In some examples, the flexible shaft length 111 can be in a range between 2 and 10 inches.

The flexible shaft 110 can be adapted to bend from the unbent state to the bent state or the bent state to the unbent state while transmitting torque from the coupling member 120 to the work member 130. The flexible shaft 110 can be adapted to rotate at a speed between 200-1000 revolutions per minute (RPM). The flexible shaft 110 can be adapted to rotate under a torque load in a range between 0.1 and 1.0 newton-meters (Nm).

Figure 2A:
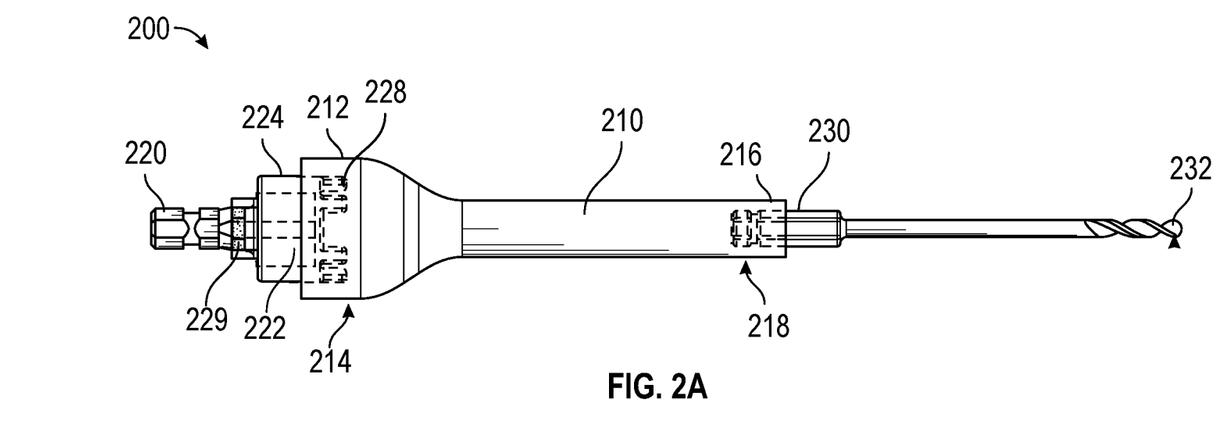
FIG. 2A is a side view of another illustrative flexible drive shaft assembly, in accordance with at least one example.
Figure 2B:
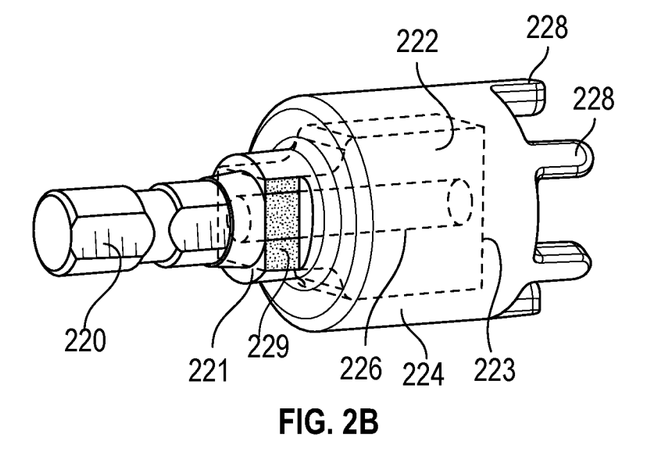
FIG. 2B is a perspective view of an illustrative coupling member of the flexible drive shaft assembly of FIG. 2A, in accordance with at least one example.

FIG. 2A shows a side view of another illustrative example of a flexible drive shaft assembly 200 for preparing a bone. FIG. 2B shows a perspective view of an illustrative coupling member 220 of the flexible drive shaft assembly 200. Like numerals may represent like elements, therefore all elements may not be described in further detail.

As shown in the illustrative example of a flexible drive shaft assembly 200 of FIG. 2A (hereinafter assembly 200), a flexible shaft 210 can extend from the coupling member 220 to a work member 230. The flexible shaft 210 can include a first overmolded connection 212 at a first end portion 214 of the flexible shaft 210 and a second overmolded connection 216 at the second end portion 218 of the flexible shaft 210. The first overmolded connection 212 can include an overmold of the flexible shaft 210 onto the coupling member 220. The second overmolded connection 216 can include an overmold of the flexible shaft 210 onto the work member 230. Between the first and second overmolded connections 212, 216, the flexible shaft 210 can be formed as a continuous, solid shaft formed by an overmolding process.

Also shown in FIG. 2A, as well as the perspective view of the coupling member in FIG. 2B, the coupling member 220 can include a central load carrying body 222 coupled to an outer locating body 224. The central load carrying body 222 can be adapted to carry the majority of a load received from a torque-providing driving tool, while the outer locating body 224 provides the interface for the torque-providing driving tool and connection to the flexible shaft 210.

The outer locating body 224 can include locating elements 228, such as fingers, to facilitate locating and orienting the coupling member 220 relative to other components of the flexible drive shaft assembly 200. The locating elements 228 can help locate outer locating body 224 relative to at least one of the flexible shaft 210, the work member 230, the central load carrying body, and the mold in which the assembly 200 is manufactured. The locating elements 228 can be provided in the shape of fingers or extensions. The additional surface area provided by the locating elements 228 also provides increased surface area for the overmolded material of the flexible shaft 210 to attach to.

In some examples, the central load carrying body 222 can be formed of a first material, and the outer locating body 224 can be formed of a second material. The first material can be a strong, rigid material such as a material including a metal. In an example where the central load carrying body 222 carries the majority of the load received, the outer locating body 224 can be formed of a second, less expensive material such as polymer having lower strength and/or rigidity characteristics than the first material.

In some examples, the central load carrying body 222 can extend from a first end portion 221 to a second end portion 223 and can include an aperture 226 extending therethrough.

In some examples, the central load carrying body 222 can be completely or partially covered by the outer locating body 224, which can be molded around the central load carrying body 222. The aperture 226 can provide improved flow of polymeric material around and through the central load carrying body 222 when molding the outer locating body 224 around the central load carrying body 222. The aperture 226 also provides additional surface area for the attachment between the central load carrying body 222 and the outer locating body 224, which increases the overall strength of the coupling member 220.

As shown in FIGS. 2A and 2B, a portion of the central load carrying body 222 can remain exposed (e.g., not covered by the outer locating body 224). For example, a coupling interface 229 of the central load carrying body 222 can remain exposed in order to provide a strong surface for the torque-providing drive tool to interface with. The coupling interface 229 receives torque from the torque-providing driving tool and transmits the torque to the outer locating body 224 and the flexible shaft 210.

In some examples, the coupling member 220 and the work member 230 can be formed of materials that are stronger and more rigid than the polymeric material that is used to form the flexible shaft 210. The coupling member 220 and work member 230 can be formed of different materials, the same material or at least one of the same materials. More rigid can be defined as having a higher bending stiffness and/or modulus of elasticity.

As shown in FIG. 2A, the work member 230 can include a work element 232 such as a drill bit. However, in some examples, as shown and described in FIG. 3, the work member 230 does not necessarily include the work element 232, but instead can be configured to interface and be coupled to one or more work elements 232 such as the drill bit shown in FIG. 2A. In some examples, the work member 230 can also be couplable to a reamer, burr or other rotating work element.

Figure 3:
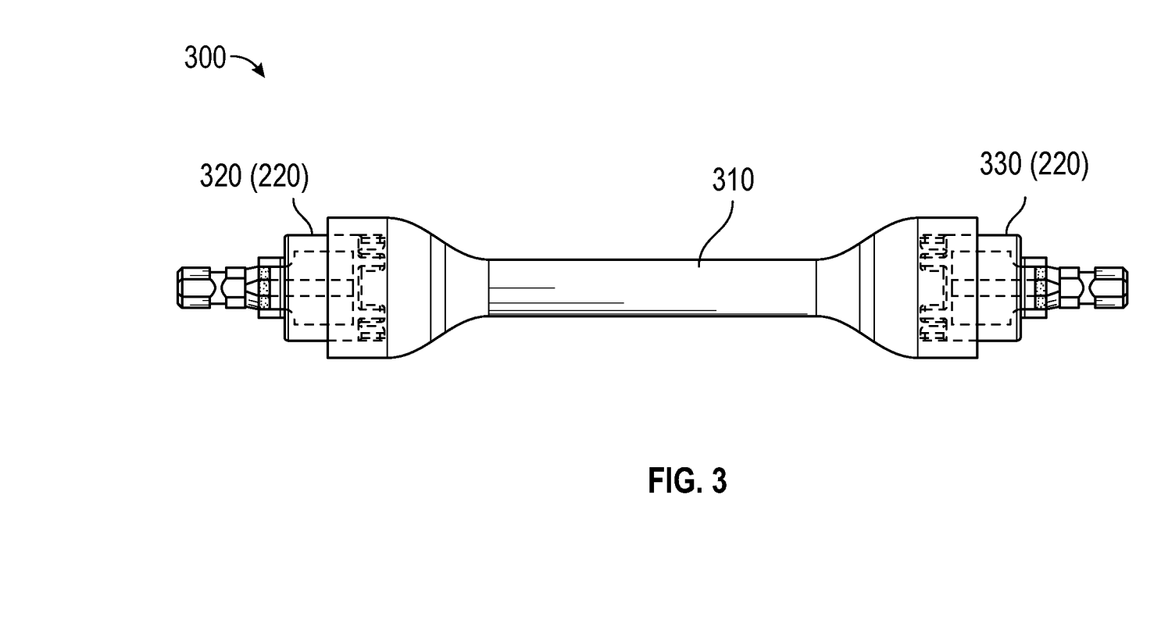
FIG. 3 is a side view of another illustrative flexible drive shaft assembly in accordance with at least one example.

FIG. 3 shows a side view of another illustrative example of a flexible drive shaft assembly 300 (hereinafter assembly 300). The assembly 300 includes an example of a modular design. Like numerals may represent like elements, therefore all elements may not be described in further detail.

As shown in FIG. 3, to improve modularity of an orthopedic tool, the flexible drive shaft assembly 300 (hereinafter assembly 300) can include a flexible shaft 310 extending between two modular connectors (e.g., 320, 330). In the example of FIG. 3, a coupling member 320 and a work member 330 can both be modular connectors that are similar to or the same as each other. For example, both the coupling member 320 and the work member 330 can be provided as the coupling member 220 of FIG. 2. This type of modular system reduces complexity and manufacturing cost.

The assembly 300 provides the advantage that the same flexible shaft 310 can be used with different work elements (e.g., drill bit 232, FIG. 2A, but also a burr or a reamer type work element). Because the same flexible shaft 310 can be used with different work elements, the flexible shaft 310 can be used to perform different steps of a surgical procedure, and the number of flexible drive shafts 310 that are needed to perform a surgical procedure can also be reduced.

In addition to being able to perform multiple steps in a particular surgical procedure, the modular assembly 300 can also be used to perform a variety of different surgical procedures. In other words, the modular assembly 300 does not need to be a dedicated tool restricted to performing a particular step of a surgical procedure or even a particular surgical procedure. The modular design allows the assembly 300 to become a universal type of tool with many applications.

The example methods described herein are directed to methods of forming an orthopedic tool such as a flexible drive shaft assembly. The methods can be described with reference to the example assemblies 100, 200 and 300 of FIGS. 1A-1C, 2A, 2B, and 3. The example methods 400 and 500 described herein are merely illustrative in nature. Although the methods 400 and 500 can be used with the example assemblies 100, 200 and 300 of FIGS. 1A-1C, 2A, 2B and 3, the methods 400 and 500 can also be used with other assemblies. Likewise, the example assemblies 100, 200 and 300 of FIGS. 1A-1C, 2A, 2B and can be used with other methods. The example methods 400 and 500 are not limited to the steps specified herein. The methods 400 and 500 can include fewer steps or additional method steps other than those described in this disclosure. Steps from methods 400 and 500 are also interchangeable and combinable.

Figure 4:
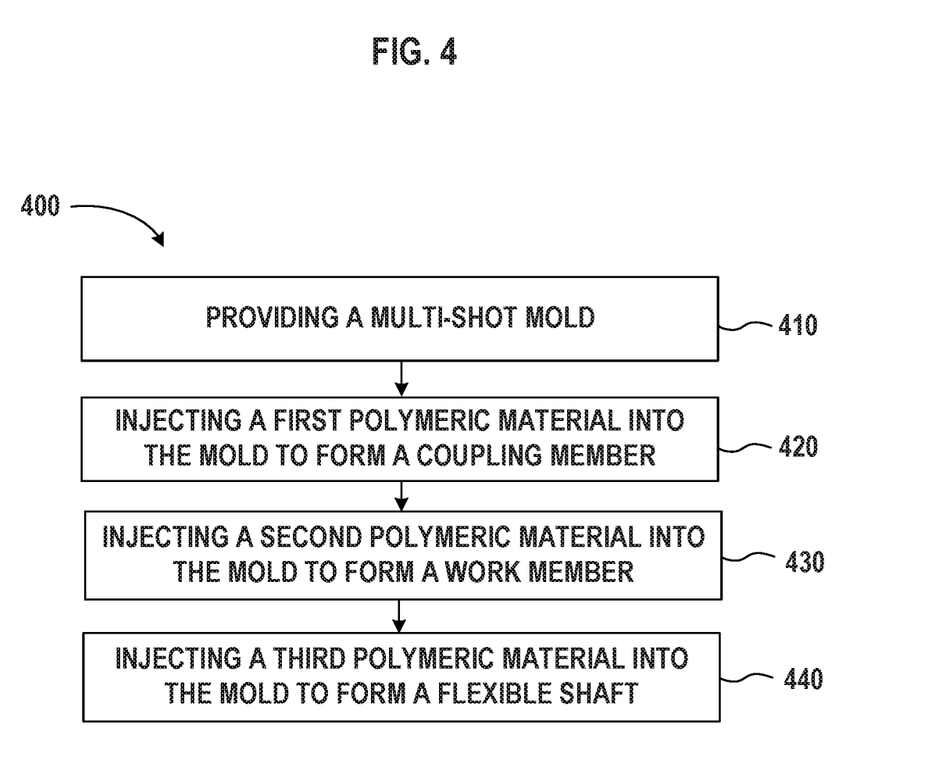
FIG. 4 is a method of manufacturing an orthopedic tool for preparing a bone, in accordance with at least one example.

FIG. 4 shows a flow chart illustrating a method 400 of manufacturing a flexible drive shaft assembly (hereinafter assembly 400). In step 410, the method 400 can include providing, receiving or manufacturing a mold. In some examples, the mold can be a single-shot mold or a multi-shot mold. In the example of a multi-shot mold, the multi-shot mold is capable of performing a method including two or more types of polymeric material that can be molded to form one component. In multi-shot molding, the different types of polymeric materials from two or more polymer injection units are injected into the mold through independent nozzles to form one molded part. Multi-shot molding creates a bond between the two types of polymer materials.

Step 420 can include providing or receiving a first polymeric material to the mold to form a coupling member. The coupling member can be adapted for attachment to a torque-providing driving tool.

In some examples, providing, receiving or manufacturing the coupling member in step 420 can include providing, receiving a coupling member including a central load carrying body comprising a first material and attaching an outer locating body around the central load carrying body. The outer locating body can include a second material different from the first material. The central load carrying body can be adapted to carry a majority of the load received from the torque-providing driving tool. The outer locating body can be adapted to locate (e.g., orient) the outer locating body relative to at least one of the central load carrying body, the work member, the flexible shaft, and the mold.

In some examples, providing or receiving the coupling member can also include inserting the central load carrying body into the mold and injecting the second material into the mold to form the outer locating body around the central load carrying body.

Step 430 can include injecting a second polymeric material into the mold to form a work member. The work member can be adapted to interface with a work element or can include a work element to interface directly with a bone, to prepare a bone in a surgical procedure. In some examples, the work element can be a drill bit and the work member can be adapted to interface with the bone directly to drill a hole in the bone. The work member can also be adapted to otherwise prepare the bone by reaming, burring or another process utilizing rotational motion of the work element to prepare bone. The first and second polymeric materials can be different materials, the same material, or include at least one of the same materials. Suitable first and second polymeric materials can include, but are not limited, to high performance reinforced polyamides and other strong polymeric materials.

Step 440 can include injecting a third polymeric material into the mold to form a flexible shaft. The third polymeric material can be an overmold type of molding process. The flexible shaft can extend from a first overmold connection to a second overmold connection. The first overmold connection can be to the coupling member at a first end portion of the flexible shaft. The second overmold connection can be to the work member at the second end portion of the flexible shaft.

In some examples, injecting the third polymeric material into the mold to form the flexible shaft in step 440 can include forming a solid polymeric shaft during an overmolding process. In some examples the flexible shaft can be formed entirely by this overmolding process. For example, the solid polymeric shaft can include a continuous overmolded polymeric shaft extending from the coupling member to the work member. The resulting flexible shaft can be adapted to transmit a majority of a rotational motion and torque received by the coupling member from a torque-providing driving tool through the flexible shaft to the work member. In some examples, the third polymeric material can transfer all, substantially all, or a majority of the rotational motion and torque from the coupling member to the work member.

Transmitting substantially all of the rotational motion and torque can be defined as transmitting 90-100% of the torque. In a more preferred embodiment, substantially all can include transmitting 95-100% of the torque. In an ideal example, excluding loss due to heat and other energy losses, the flexible shaft can transmit 100% of the torque.

In some examples, the first and second polymeric material(s) of steps 420 and 430 can be more rigid than the third polymeric material of step 440. More rigid can be defined as having a higher bending stiffness and/or modulus of elasticity.

Figure 5:
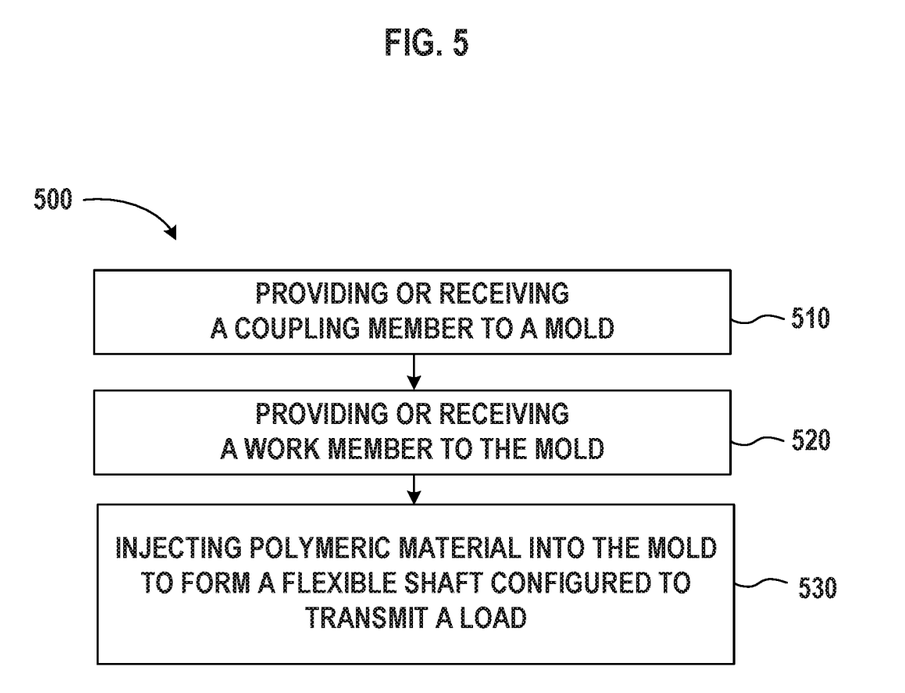
FIG. 5 is another method of manufacturing an orthopedic tool for preparing a bone in accordance with at least one example.

FIG. 5 shows another illustrative method 500 for providing, receiving or manufacturing a flexible drive shaft assembly (hereinafter assembly 500) for preparing a bone. In some examples, steps from the method 400 can be included in the method 500 or interchanged with steps of the method 500.

In an example, step 510 can include providing or receiving a coupling member to a mold, the coupling member adapted for attachment to a torque-providing driving tool. The coupling member can include any of the features described herein including the features described with respect to the coupling member 120, 220, 320 of assemblies 100, 200, 300 and step 420 of the method 400. The mold can include either a single-shot mold or a multi-shot mold.

Step 520 can include providing or receiving a work member to the mold, the work member adapted to interface with the bone to prepare the bone. The work member can include any of the features described herein including the features described with respect to the work members 130, 230, 330 of assemblies 100, 200, 300 and step 430 of the method 400.

Step 530 can include injecting a polymeric material into the mold to form a flexible shaft extending from a first overmold connection to the coupling member to a second overmold connection to the work member. The first overmold connection can be located at a first end portion of the flexible shaft, and the second overmold connection can be located at a second end portion of the flexible shaft. Injecting the polymeric material in step 530 can result in molding of a flexible shaft that can be adapted to transmit all, substantially all or a majority of the rotational motion and torque received by the coupling member from the torque-providing driving tool to the work member. Injecting polymeric material into the mold in step 530 can include forming a solid, continuous polymeric shaft during an overmolding process.

In the example where the method 500 can be performed using a single-shot mold, providing or receiving the coupling member and the work member to the mold can include inserting the coupling member and the work member into the mold. In the example where the method 500 can be performed using a multi-shot mold, providing or receiving the coupling member and the work member to the mold can include injecting a second polymer into the mold to form at least a portion of one of the coupling member and the work member.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. In the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

NUMBERED EXAMPLES

Example 1 is a method of manufacturing an orthopedic tool for preparing a bone, the method comprising: providing, receiving or manufacturing a mold; providing or receiving a coupling member to the mold; the coupling member comprising a first polymeric material, the coupling member adapted for attachment to a torque-providing driving tool; injecting a second polymeric material into the mold to form a work member, the work member adapted to interface with the bone to prepare the bone; and injecting a third polymeric material into the mold to form a flexible shaft extending from a first overmold connection to the coupling member at a first end portion of the flexible shaft to a second overmold connection to the work member at a second end portion of the flexible shaft; wherein the flexible shaft is adapted to transmit a majority of a rotational motion and torque received by the coupling member from the torque-providing driving tool through the flexible shaft to the work member.

In Example 2, the subject matter of Example 1 includes, wherein injecting the third polymeric material into the mold to form the flexible shaft comprises forming a solid polymeric shaft during an overmolding process.

In Example 3, the subject matter of Examples 1-2 includes, wherein injecting the third polymeric material into the mold to form the flexible shaft comprises forming a continuous polymeric shaft extending from the coupling member to the work member.

In Example 4, the subject matter of Examples 1-3 includes, wherein the third polymeric material is adapted to transmit substantially all the rotational motion and torque from the coupling member to the work member.

In Example 5, the subject matter of Examples 1-4 includes, wherein the first polymeric material and the second polymeric material are the same type of polymeric material.

In Example 6, the subject matter of Examples 1-5 includes, wherein the first and second polymeric material are more rigid than the third polymeric material.

In Example 7, the subject matter of Examples 1-6 includes, wherein providing or receiving the coupling member includes inserting a central load carrying body into the mold and injecting the second polymeric material into the mold to form an outer locating body.

In Example 8, the subject matter of Examples 1-7 includes, wherein providing or receiving the coupling member comprises providing or receiving a central load carrying body comprising a first material and attaching an outer locating body around the central load carrying body comprising a second material, wherein the central load carrying body is adapted to carry the majority of a load received from the torque-providing driving tool, and wherein the outer locating body is adapted to orient the coupling member relative to the work member.

Example 9 is a method of manufacturing an orthopedic tool for preparing a bone, the method comprising: providing or receiving a coupling member to a mold, the coupling member adapted for attachment to a torque-providing driving tool; providing or receiving a work member to the mold, the work member adapted to interface with the bone to prepare the bone; and injecting a polymeric material into the mold to form a flexible shaft extending from a first overmold connection to the coupling member at a first end portion of the flexible shaft to a second overmold connection to the work member at a second end portion of the flexible shaft; wherein the flexible shaft is adapted to transmit a majority of a rotational motion and torque received by the coupling member from the torque-providing driving tool through the flexible shaft to the work member.

In Example 10, the subject matter of Example 9 includes, wherein injecting polymeric material into the mold to form the flexible shaft comprises forming a solid, continuous polymeric shaft during an overmolding process.

In Example 11, the subject matter of Examples 9-10 includes, wherein the polymeric material is adapted to transmit substantially all the rotational motion and torque from the coupling member to the work member.

In Example 12, the subject matter of Examples 9-11 includes, wherein the mold is a multi-shot mold configured to mold the coupling member, the work member and the flexible shaft, and wherein providing at least one of the coupling member and the work member to the mold comprises injecting a second polymer into the mold to form at least one of the coupling member and the work member.

Example 13 is a flexible orthopedic tool for preparing a bone of a patient, the flexible orthopedic tool comprising: a flexible shaft having a length extending from a first end portion to a second end portion, the flexible shaft comprising a polymeric material adapted to bend into a curved shape; a coupling member coupled to the first end portion, the coupling member adapted for attachment to a torque-providing driving tool, the coupling member adapted to receive a rotational motion and torque from the torque-providing driving tool and to transmit the rotational motion and torque through the flexible shaft; and a work member coupled to the second end portion, the work member adapted to receive the rotational motion and torque from the flexible shaft and to interface with the bone or a work element configured to prepare the bone, wherein the polymeric material is adapted to carry and transmit substantially all of the rotational motion and torque from the coupling member to the work member.

In Example 14, the subject matter of Example 13 includes, wherein the flexible shaft comprises a solid polymeric shaft formed by overmolding.

In Example 15, the subject matter of Examples 13-14 includes, wherein the flexible shaft comprises a continuous shaft extending from a first overmolded connection to the coupling member, to a second overmolded connection to the work member.

In Example 16, the subject matter of Examples 13-15 includes, wherein the flexible shaft is adapted to bend from an unbent state to a bent state or the bent state to the unbent state while transmitting rotational motion and torque.

In Example 17, the subject matter of Examples 13-16 includes, wherein the coupling member comprises a central load carrying body coupled to an outer locating body, wherein the central load carrying body is adapted to carry a majority of a load received from the torque-providing driving tool, and wherein the outer locating body is adapted to locate the coupling member relative to the work member.

In Example 18, the subject matter of Example 17 includes, wherein the central load carrying body is formed of a first material, and wherein the outer locating body is formed of a second polymeric material that is more rigid than the polymeric material of the flexible shaft.

In Example 19, the subject matter of Examples 13-18 includes, inches.

In Example 20, the subject matter of Examples 13-19 includes, newton-meters (Nm).

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

What is claimed is:

1. A method of manufacturing an orthopedic tool for preparing a bone, the method comprising:
   providing, receiving or manufacturing a mold;
   providing or receiving a coupling member to the mold, the coupling member comprising a first polymeric material, the coupling member adapted for attachment to a torque-providing driving tool;
   injecting a second polymeric material into the mold to form a work member, the work member adapted to interface with the bone to prepare the bone; and
   injecting a third polymeric material into the mold to form a flexible shaft extending from a first overmold connection to the coupling member at a first end portion of the flexible shaft to a second overmold connection to the work member at a second end portion of the flexible shaft;
   wherein the flexible shaft is adapted to transmit a majority of a rotational motion and torque received by the coupling member from the torque-providing driving tool through the flexible shaft to the work member, and
   wherein providing or receiving the coupling member includes inserting a central load carrying body into the mold and injecting the second polymeric material into the mold to form an outer locating body.

2. The method of claim 1, wherein injecting the third polymeric material into the mold to form the flexible shaft comprises forming a solid polymeric shaft during an overmolding process.

3. The method of claim 1, wherein injecting the third polymeric material into the mold to form the flexible shaft comprises forming a continuous polymeric shaft extending from the coupling member to the work member.

4. The method of claim 1, wherein the third polymeric material is adapted to transmit substantially all the rotational motion and torque from the coupling member to the work member.

5. The method of claim 1, wherein the first polymeric material and the second polymeric material are a same type of polymeric material.

6. The method of claim 1, wherein the first and second polymeric material are more rigid than the third polymeric material.

7. The method of claim 1, wherein the central load carrying body is adapted to carry a majority of a load received from the torque-providing driving tool, and wherein the outer locating body is adapted to orient the coupling member relative to the work member.

8. A method of manufacturing an orthopedic tool for preparing a bone, the method comprising:
   providing or receiving a coupling member to a mold, the coupling member adapted for attachment to a torque-providing driving tool;
   providing or receiving a work member to the mold, the work member adapted to interface with the bone to prepare the bone; and
   injecting a polymeric material into the mold to form a flexible shaft extending from a first overmold connection to the coupling member at a first end portion of the flexible shaft to a second overmold connection to the work member at a second end portion of the flexible shaft;
   wherein the flexible shaft is adapted to transmit a majority of a rotational motion and torque received by the coupling member from the torque-providing driving tool through the flexible shaft to the work member, and
   wherein providing or receiving the coupling member includes inserting a central load carrying body into the mold and injecting a second polymeric material into the mold to form an outer locating body.

9. The method of claim 8, wherein the polymeric material is adapted to transmit substantially all the rotational motion and torque from the coupling member to the work member.

10. The method of claim 8, wherein the central load carrying body is adapted to carry a majority of a load received from the torque-providing driving tool, and wherein the outer locating body is adapted to orient the coupling member relative to the work member.

11. The method of claim 8, wherein injecting polymeric material into the mold to form the flexible shaft comprises forming a solid, continuous polymeric shaft during an overmolding process.

\* \* \* \* \*